(12) United States Patent
Svanberg et al.

(10) Patent No.: US 7,037,325 B2
(45) Date of Patent: May 2, 2006

(54) THERAPY AND DIAGNOSIS SYSTEM AND METHOD WITH DISTRIBUTOR FOR DISTRIBUTION OF RADIATION

(75) Inventors: Sune Svanberg, Lund (SE); Stefan Andersson-Engels, Hoor (SE); Katarina Svanberg, Lund (SE)

(73) Assignee: SpectraCure AB, Veberod (SE)

( * ) Notice: Subject to any disclaimer, the term of this patent is extended or adjusted under 35 U.S.C. 154(b) by 0 days.

(21) Appl. No.: 10/495,709

(22) PCT Filed: Nov. 11, 2002

(86) PCT No.: PCT/SE02/02050

§ 371 (c)(1),
(2), (4) Date: Aug. 16, 2004

(87) PCT Pub. No.: WO03/041575

PCT Pub. Date: May 22, 2003

(65) Prior Publication Data

US 2004/0260366 A1      Dec. 23, 2004

(30) Foreign Application Priority Data

Nov. 14, 2001   (SE) .................................. 0103771

(51) Int. Cl.
*A61N 5/06* (2006.01)
(52) U.S. Cl. ............................ 607/89; 128/898; 607/88
(58) Field of Classification Search ................ 128/898; 607/89
See application file for complete search history.

(56) References Cited

U.S. PATENT DOCUMENTS

| 5,989,181 A * | 11/1999 | Dutting et al. ............... 600/108 |
| 6,048,359 A * | 4/2000 | Biel ............................. 607/92 |
| 6,128,525 A * | 10/2000 | Zeng et al. .................. 600/476 |
| 6,210,425 B1 * | 4/2001 | Chen ............................ 607/88 |
| 6,214,033 B1 * | 4/2001 | Ii et al. ........................ 607/89 |
| 6,603,988 B1 * | 8/2003 | Dowlatshahi ............... 600/407 |
| 2003/0036785 A1 * | 2/2003 | Ii et al. ........................ 607/89 |

FOREIGN PATENT DOCUMENTS

| EP | 0195375 | 9/1986 |
| JP | 63 060421 | 8/1988 |
| JP | 4 343317 | 4/1993 |

* cited by examiner

*Primary Examiner*—Michael F Peffley
*Assistant Examiner*—Henry M Johnson, III
(74) *Attorney, Agent, or Firm*—Knobbe Martens Olson & Bear LLP

(57) ABSTRACT

A distributor for a system for interactive interstitial photodynamic and photothermal tumor therapy and tumor diagnosis, comprises a plurality of primary radiation conductors arranged for conducting radiation to and from the tumor site, a plurality of secondary radiation conductors, two flat discs abutting against each other, wherein a first of said discs is fixed and the second of said discs is turnable relatively to the other disc, and each disc has holes arranged on a circular line. The proximal ends of the primary radiation conductors are fixed in the holes of the fixed disc and distal ends of the secondary radiation conductors are fixed in the holes of the turnable disc, whereby the primary and the secondary radiation conductors by rotation of the turnable disc are connectable to each other in different constellations.

20 Claims, 3 Drawing Sheets

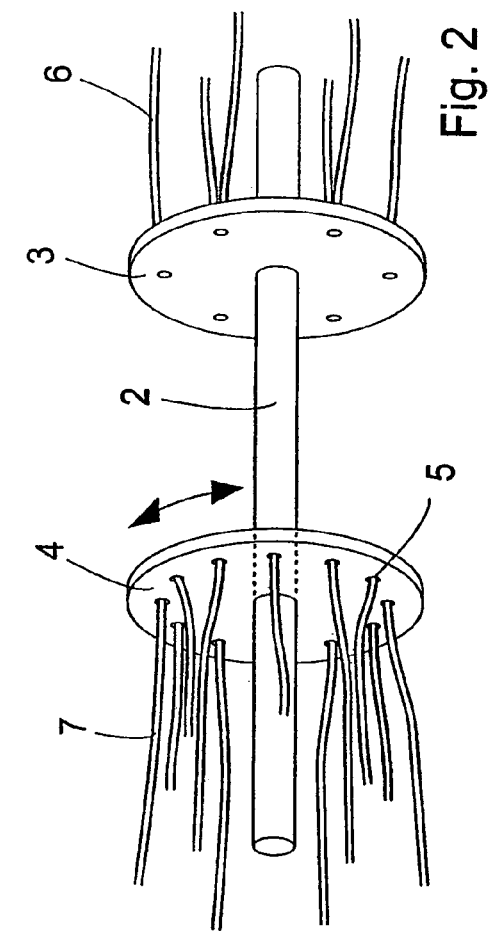
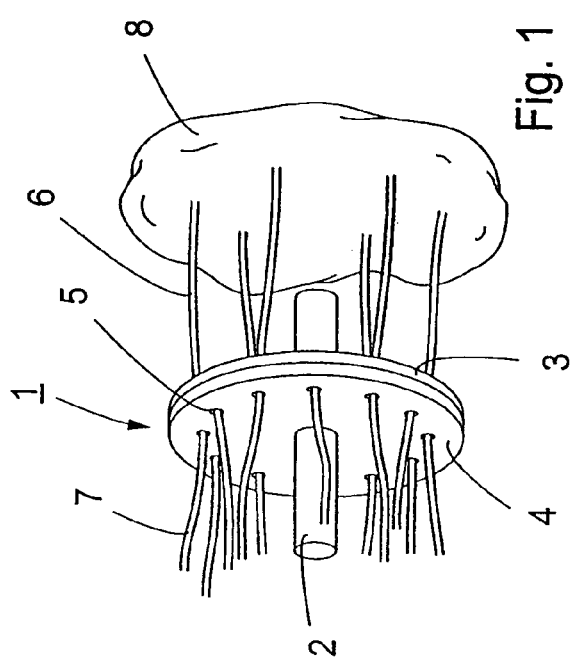
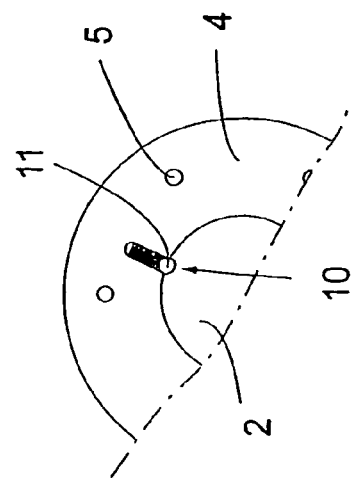
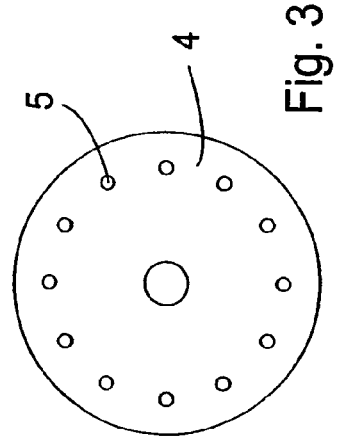

THERAPY AND DIAGNOSIS SYSTEM AND METHOD WITH DISTRIBUTOR FOR DISTRIBUTION OF RADIATION

BACKGROUND OF THE INVENTION

The invention relates to a system and a method for interstitial photodynamic and photothermal tumor therapy and diagnosis of a tumor at a tumor site in a body, wherein radiation is conducted to the site for said therapy and diagnosis. The system comprises a distributor of radiation from at least one therapeutic radiation source and a diagnostic radiation source to said tumor, and from the tumor to at least one radiation sensor, respectively.

Within the field of medical therapy of tumor diseases, a plurality of treatment modalities has been developed for the treatment of malignant tumor diseases, e.g. a tumefaction. Operation, cytostatics treatment, treatment with ionising radiation (gamma or particle radiation), isotope therapy, and brachy therapy employing radioactive needles are examples of common treatment modalities. In spite of great progress within therapy, the tumor diseases continue to account for much human suffering, and are responsible for a high percentage of deaths in Western countries. A relatively new treatment modality, photodynamic therapy, commonly abbreviated PDT, provides an interesting complement or alternative in the treatment field. A tumorseeking agent, normally referred to as a sensitizer, is administered to the body intravenously, orally or topically. It accumulates in malignant tumors to a higher extent than in the surrounding healthy tissue. The tumor area is then irradiated with non-thermal red light, normally from a laser, leading to excitation of the sensitizer to a more energetic state. Through energy transfer from the activated sensitizer to the oxygen molecules of the tissue, the oxygen is transferred from its normal triplet state to the excited singlet state. Singlet oxygen is known to be particularly toxic to tissue; cells are eradicated and the tissue goes in necrosis. Because of the localization of the sensitizer to tumor cells a unique selectivity is obtained, where surrounding healthy tissue is spared. The initial clinical experience, using in particular haematoporphyrin derivative (HPD) and delta amino levulinic acid (ALA) are good.

Sensitizers also exhibit a further useful property; to yield a characteristic red fluorescence signal when the substance is excited with violet or ultraviolet radiation. This signal clearly appears in contrast to the autofluorescence of the tissue and can be used to localize tumors and for quantifying the size of the uptake of the sensitizer in the tissue.

The limited penetration in the tissue of the activating red radiation is a big drawback of PDT. The result is that only tumors up to about 5 mm thickness can be treated by surface irradiation. In order to treat thicker and deep-lying tumors, interstitial PDT (IPDT) can be utilized. Here, light-conducting optical fibers are brought into the tumor using, e.g. a syringe needle, in the lumen of which a fiber has been placed.

In order to achieve an efficient treatment, several fibers have been used to ascertain that all tumor cells are subjected to a sufficient dose of light so that the toxic singlet state is obtained. It has been shown to be achievable to perform dose calculations of the absorptive and scattering properties of the tissue. E.g., in the Swedish patent SE 503 408 an IPDT system is described, where six fibers are used for treatment as well as for measurement of the light flux which reaches a given fiber in the penetration through the tissue from the other fibers. In this way an improved calculation of the correct light dose can be achieved for all parts of the tumor.

In the equipment described in SE 503 408 the light from a single laser is divided up in six different parts using a beamsplitter system comprising a large number of components. The light is then focused into each of the six individual treatment fibers. One fiber is used as a transmitter while the other fibers are used as receivers of radiation penetrating the tissue. For light measurement light detectors are swung into the beam path which thus is blocked, and the weak light, which originates from the fibers that collected the light which is administered to the tissue, is measured.

However, such open beam paths result in a strongly lossy beamsplitting and the resulting losses of light drastically impair the light distribution as well as the light measurement. Furthermore, such a system must often be adjusted optically, which is also an important consideration in connection with clinical treatments.

SUMMARY OF THE INVENTION

In one embodiment, the invention comprises a system for interactive interstitial photodynamic or photothermal tumor therapy and tumor diagnosis, comprising at least one therapeutic radiation source and at least one diagnostic radiation source, at least one diagnostic radiation sensor, and at least two primary radiation conductors which at their distal ends are interstitially arranged in a tumor site, wherein the primary radiation conductors in use are employed as a transmitter for diagnostic radiation from said diagnostic radiation source for diagnosis of a tumor at said tumor site, or for therapeutic radiation from said therapeutic radiation source for therapy of the tumor, respectively or as a receiver for conduction of radiation from the tumor site for diagnosis of the tumor at the tumor site, and a distributor for distribution of radiation from the diagnostic and therapeutic radiation source to the tumor site, and from the tumor site to at least one diagnostic radiation sensor. In preferred embodiments, the distributor comprises a plurality of primary radiation conductors arranged for conducting radiation to and from the tumor site, a plurality of secondary radiation conductors arranged for delivering radiation from the diagnostic or therapeutic radiation source or conduction of radiation to the diagnostic radiation sensor, two flat discs abutting against each other, wherein a first of said discs is fixed and the second of said discs is turnable relatively to the other disc, and wherein each disc has holes arranged on a circular line. The proximal ends of the primary radiation conductors are fixed in the holes of the first disc and distal ends of the secondary radiation conductors are fixed in the holes of the second disc, whereby the primary and the secondary radiation conductors by rotation of the two discs relative another are connectable to each other in different constellations.

In another embodiment, a method for interactive interstitial photodynamic or photothermal tumor therapy and diagnosis. The method preferably comprises inserting at least two primary radiation conductors at distal ends thereof interstitially into a tumor, activating a diagnostic radiation source and transmitting diagnostic radiation through one of said primary radiation conductors to the distal ends thereof, transmitting the diagnostic radiation through tissue at said tumor site to distal ends of the remaining primary radiation conductors, collecting and evaluating diagnostic information from radiation received from said tumor, automatically switching between tumor therapy and tumor diagnostics, and controlling the tumor therapy by regulating a therapeutical radiation intensity depending on said diagnostic information.

BRIEF DESCRIPTION OF THE DRAWINGS

In order to more closely explain the invention a number of embodiments of the invention will be described in the following with reference to the figures, wherein FIG. 1 is a schematic perspective view of a first embodiment of the system according to the invention, wherein light conductors arranged in said invention are interstitially inserted in a tumor, FIG. 2 is a view similar to FIG. 1, where the discs of the distributor are brought apart, FIG. 3 is a planar view from above of the turnable distributor disc with holes arranged in said disc, FIG. 4 is a fragmentary cross section view of the turnable disc of said distributor, wherein a springloaded ball is provided.

DETAILED DESCRIPTION OF THE INVENTION

Figure 5:
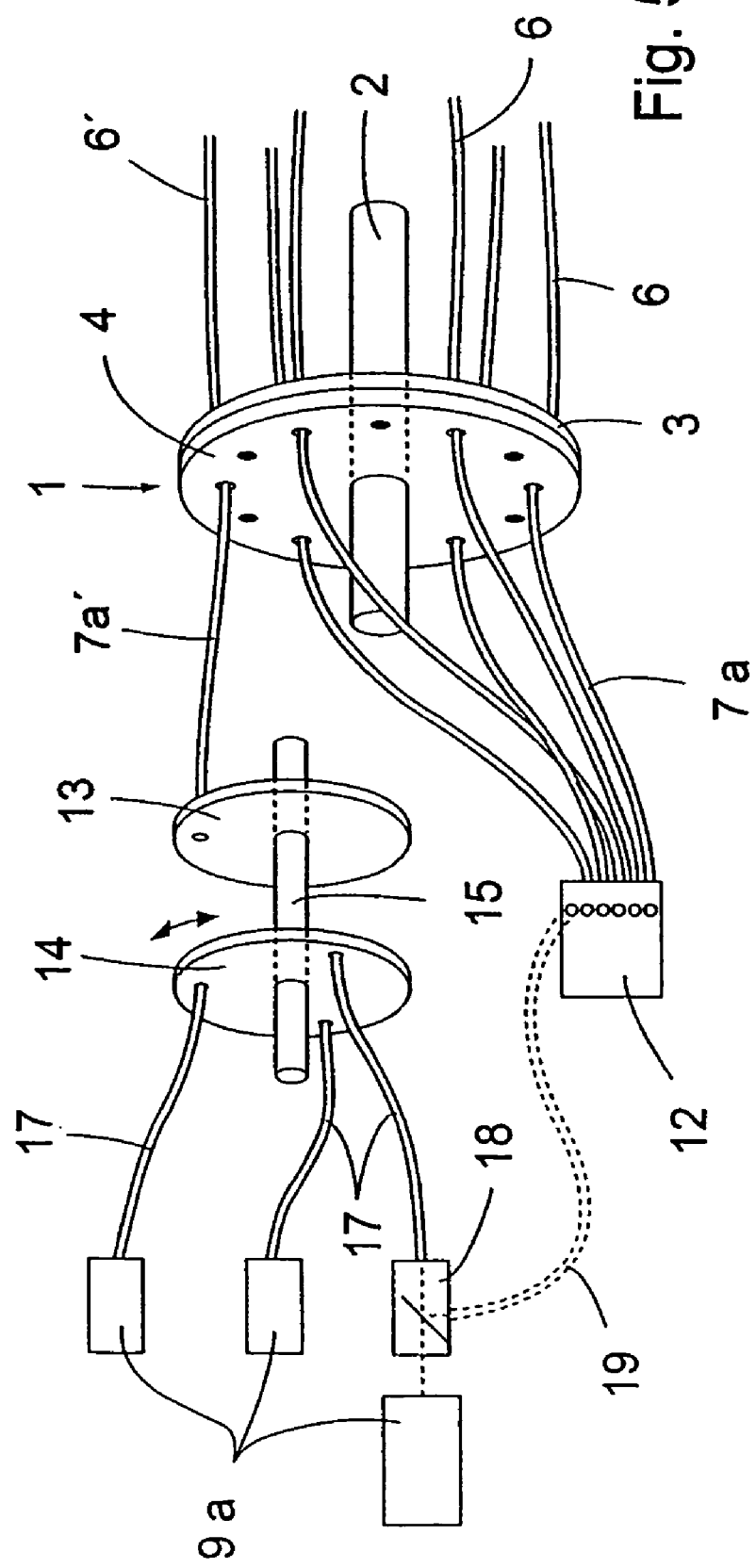
FIG. 5 is a schematic perspective view illustrating the use of the system according to the invention with the distributor in the mode of tumor diagnostics.

A preferred embodiment of the distributor of the system according to the invention is now described with reference to FIG. 14. The distributor 1 comprises two flat and in proximity lying discs made of, e.g. 1 cm thick steel. The discs are hereby arranged on an axis 2, wherein one of the discs is a fixed disc 3 and the other one is a turnable disc 4. The discs 3 and 4 are abutting against each other in FIG. 1 and separated from each other in FIG. 2.

Evenly distributed holes 5 lying on a circle are arranged in both discs (FIG. 3) for fixation of primary radiation conductors 6 in one of the discs and secondary radiation conductors 7 in the other disc, respectively. Preferably the diameter of the holes is 0.3–0.7 mm. In order to attain a high precision, allowing the light conductors to be arranged exactly face to face, the holes of the two discs can be drilled together, maybe with a centering tube. Then the common axis 2 is utilized. It is thus possible to achieve a very high precision when making the series of holes.

By employing discs drilled together, radiation conductors can be fixed in said discs, wherein an extra, thinner disc then can be turned slightly, preferably springloaded, so that all light conductors are simultaneously pinched in their positions without the need for any glue or other fixation means. Alternatively, the diameter of the holes is made larger than the diameter of the light conductors, wherein the holes can be dressed with an appropriate piece of tubing, or the ends of the light conductors can be supplied with a fitted hose. Alternatively, the ends of the light conductors can be flared or flanged into the holes.

Preferably the light conductors are optical fibers, wherein different types of hoses or flexible tubes containing a light-conducting material are included. The light conductors should have such a length and be arranged in such a way that the turnable disc 4 can be turned without problems a full turn (360 degrees). The direction of movement can be reversed to avoid the light conductors forming a spiral.

According to the invention a plurality of primary light conductors 6 in a system are arranged in the fixed disc 3 for conduction of radiation to and from a reaction site 8. By a reaction site we in the present context mean a site where photodynamically active compounds will react in a tumor when subject to therapy. E.g., by being forwarded through the lumen of injection needles which are placed in the tumor, these primary radiation conductors 6 are then fixed in the reaction site 8. Then the primary radiation conductors are moved forward to arrive outside the distal end of the needle. The same light conductor 6 is used all the time for integrated diagnostics and dosimetry, to avoid that the patient be subjected to multiple pricks.

The holes 5 in the fixed disc 3 as well as in the turnable disc 4 are arranged on a circular line, wherein the circle radius on one disc equals the circle radius on the other disc. The holes on one disc are equally distributed along the circle line with an angular separation of $v_1 = (360/n_1)$ degrees, where $n_1$ equals the number of holes, and the holes of the other disc are equally distributed along the circle line with an angular separation $v_2$ equalling $(360/n_2)$ degrees. The proximal ends of the primary radiation conductors 6 are fixed in the holes of the fixed disc 3, and distal ends of the secondary radiation conductors 7 are fixed in the holes of the turnable disc 4. In order to make the holes, and thereby the primary and secondary radiation conductors in both discs connectable to each other in different constellations by turning of the turnable disc 4, $n_2$ is selected to be a multiple of $n_1$, in such a way that $n_2$ is obtained as an integer larger or equal to 1. Suitably the number of holes in the fixed disc is chosen from two to more than six.

Preferably six holes are arranged in the fixed disc 3 and twelve holes are arranged in the turnable disc 4. With six primary radiation conductors 6 the angular separation will accordingly become 60 degrees in the fixed disc 3 and with twelve holes arranged in the turnable disc 4 the angular separation will become 30 degrees for the secondary radiation conductors 7.

In order to facilitate the comprehension of the invention the following description of a preferred embodiment of the distributor of the system according to the invention relates to six primary radiation conductors 6 arranged with their proximal ends in the fixed disc 3 for conduction of radiation to and from the reaction site 8 at the distal ends of the primary radiation conductors.

Thus, the turnable disc 4, as well as the fixed disc 3, have six holes 5 for corresponding six diagnostic secondary radiation conductors 7, and, in addition, six further holes for six therapeutic secondary radiation conductors 7. All these twelve radiation conductors 7 can release radiation to the reaction site 8 and receive radiation from said site. Thus, several spectra can be recorded and read out simultaneously.

By turning the turnable disc 4 the primary and the secondary radiation conductors become connectable to each other in different constellations. An exact positioning of the opposing radiation conductors in the distributor 1 is facilitated by arranging means for stopping the turnable disc 4 in predetermined angular positions. E.g., groves 10 can be arranged in the axis 2 for catching a springloaded ball 11 arranged in the turnable disc 4 (FIG. 4).

In order to allow a fast and efficient switching between a diagnostic mode and a therapeutic mode, every other of the secondary light conductors of the distributor 1 according to the invention, are divided into a diagnostics and into a therapeutic series. Both series of holes are arranged on the same circle, but displaced by 30 degrees with regard to each other. A specific therapeutic light conductor 7a' in the diagnostic series of every other secondary light conductor is arranged for emitting radiation from at least one diagnostic radiation source 9a. The other, non specific diagnostic radiation conductors 7a in the diagnostic series of secondary radiation conductors are arranged for conduction of radiation to at least one diagnostic radiation sensor 12. The therapeutic series of every other secondary radiation conductor 7b is for therapeutical purposes arranged to emit radiation to the reaction site 8 from at least one therapeutic radiation source 9b.

In the preferred embodiment of the invention, the primary and secondary radiation conductors are optical fibers, which in the distributor 1 shown in FIGS. 1 and 2 are connected to the fixed disc 3 as well as the turnable disc 4. Out of the fibers, which are connected to the turnable disc 4, six diagnostic fibers can be used for diagnostic purposes and six therapeutic fibers can be used of therapeutical purposes. However, in the diagnostic mode, from one to more than three modalities can be employed.

Figure 6:
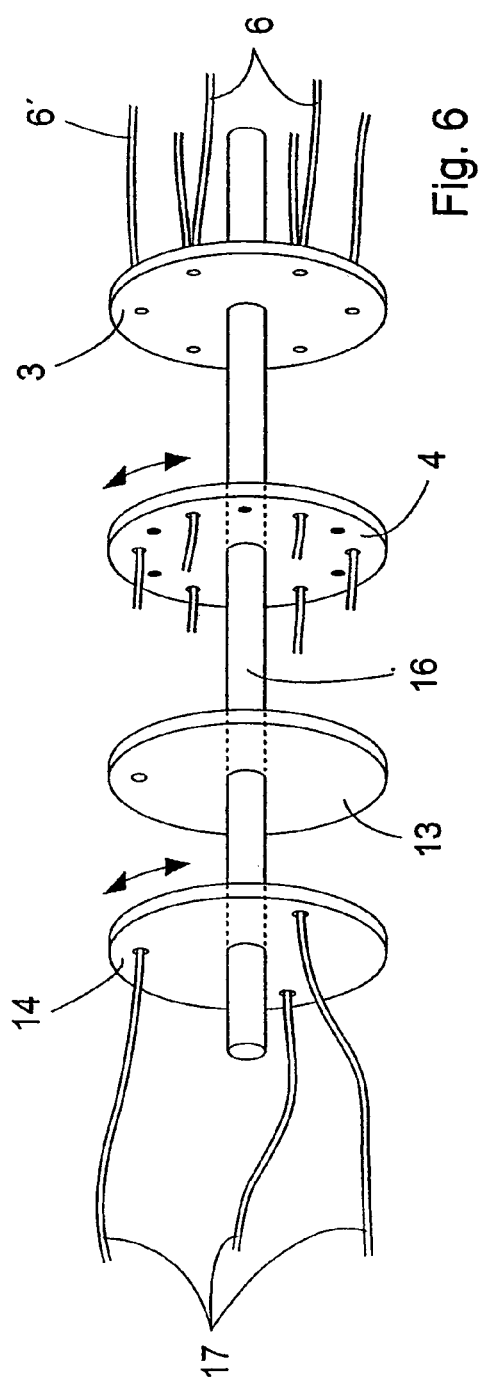
FIG. 6 is a view similar to FIG. 5 and FIG. 2, where two distributors are arranged on the same single axis.
Figure 7:
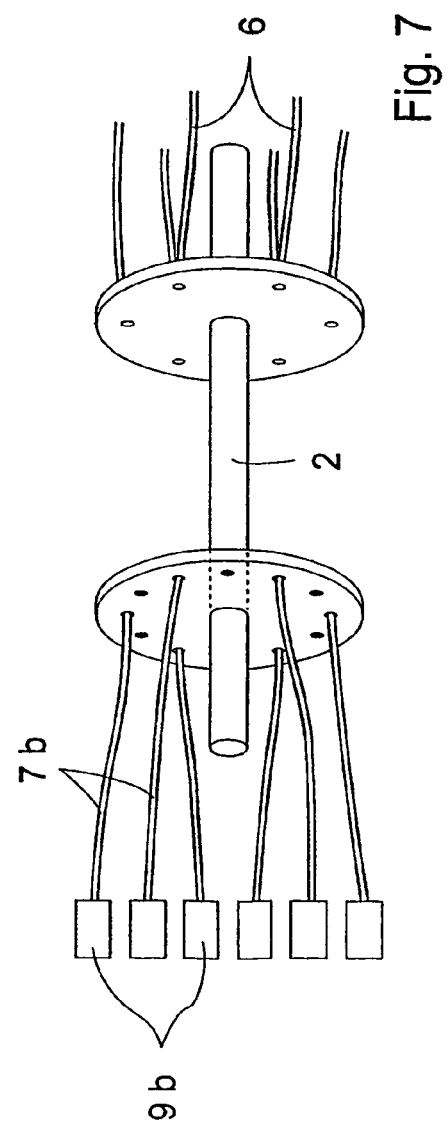
FIG. 7 is a schematic perspective view illustrating the use of the system according to the invention, with the distributor in the mode of photodynamic treatment of a tumor.

With reference to FIGS. 5–7 only the presently described radiation conductors which are coupled to a turnable disc are for clarifying purposes shown; the other radiation conductors are not shown although they are coupled to said disc.

By turning the turnable disc 4 by 30 degrees the primary fibers 6 which at their distal ends, respectively, are optically coupled to the tissue of the patient can be employed for therapy as well as diagnostics and measurements. One out of every diagnostic secondary radiation conductor 7 is in the diagnostic mode connected to different radiation sources for diagnostics, while the other five diagnostic radiation conductors receive signals, which are related to the interaction of these diagnostic radiation sources with the tissue.

Since intensity as well as spectral resolution is of interest, the distal ends of these five diagnostic radiation conductors are arranged in a slit-like arrangement so that they overlap the entrance slit and/or constitute the entrance slit of the radiation sensor 12, which is a compact spectrometer and is supplied with a two-dimensional detector array. The recording range of the spectrometer is preferably within the range 400 to 900 nm. Each of the diagnostic radiation conductors 7a can of course be connected to an individual radiation detector 12 in the form of a spectrometer or another type of detector, e.g. a compact integrated spectrometer.

With reference to FIG. 5 the specific diagnostic radiation conductor 7a' is connected to an arrangement similar to the distributor 1, which comprises a second fixed disc 13 and a second turnable disc 14 which are arranged on a common axis 15. All fixed and turnable discs can also be arranged on one single axis as is shown in FIG. 6. A more compact and robust construction is obtained in this way.

More specifically the diagnostic radiation conductor 7a' is proximally arranged in a single hole on the second fixed disc 13. Further diagnostic light conductors 17 are arranged on a circle in said second turnable disc 14; in this case three diagnostic light conductors which at their proximal end, respectively, are connected to different radiation sources 9a, and which each are connectable to the diagnostic radiation conductor 7a' and further on to a primary radiation conductor 6' comprised in the different primary radiation conductors 6 (See FIG. 5).

Preferably the diagnostic radiation source 9a is a laser of the same wavelength as the one utilized for the laser irradiation for photodynamic tumor therapy, but of substantially lower output power. Suitable filters can be arranged on the second turnable disc 14, to be turned into the light path of the diagnostic radiation sensor 12 in order to secure that the correct dynamic range is utilized for all measurement tasks.

Certain of the diagnostic radiation sources 9a are utilized in order to study how radiation (light) of the corresponding wavelength is penetrating through the tissue of the tumor. When light from a diagnostic radiation source 9a is transmitted through the particular diagnostic radiation conductors 17, 7a', 6' via the discs 14, 13, 4, 3, respectively, into the tissue 8, one of the primary radiation conductors 6, which is the radiation conductor 6' opposing the diagnostic radiation conductor 7a' in the distributor 1, will function as a transmitter into the tumor 8, and the other five primary radiation conductors 6 having their distal ends arranged in the tumor 8 will act as receivers and collect the diffuse flux of light reaching them. The light collected is again conducted via the discs 3, 4, and diagnostic radiation conductors 7a to the radiation sensor 12 and five different light intensities can be recorded on the detector array.

When the turnable disc 4 is turned by 60 degrees, the next primary radiation conductor 6 to the patient will get the role as transmitter, and the five others become the receivers for a new light distribution. After four further turns of the turnable disc 4, each by 60 degrees to the following primary radiation conductor 6 in the patient, light flux data for all remaining combinations of transmitters/receivers have been recorded. Thus, in total 6*5=30 measurement values are obtained and can be used as input data for a tomographic modelling of the optical dose build up in the different parts of the tumor during the course of the treatment.

As an alternative to a specific wavelength, radiation from a white light source can be coupled into the particular diagnostic light conductor 7a' and into the tissue from the distal end of primary radiation conductor 6'. From the distal end of primary radiation conductor 6', on passage through the tissue to the distal end of the receiving light conductor 6 in the patient, the well-defined spectral distribution of the diagnostic radiation source 9a will be modified by the tissue absorption. Then, oxygenated blood yields a different signature than non-oxygenated blood, allowing a tomographic determination of the oxygen distribution utilizing the thirty different spectral distributions which are read out, five spectra at a time in the six possible different constellations on rotation of the turnable disc 4 during a diagnostic investigation. Such a determination of the oxygenation in the tumor is important, since the PDT process requires access to oxygen in the tissue.

Finally, a light source for blue/violet or ultraviolet light, e.g. a laser, can be coupled to the particular radiation conductor 7a'. Then fluorescence is induced in the tissue, and a sensitizer administered to the tissue displays a characteristic red fluorescence distribution in the red/near-infrared spectral region. The strength of the corresponding signal allows a quantification of the concentration of the sensitizer in the tissue.

Since the short wavelength light has a very low penetration into the tissue, the induced fluorescence must be measured locally at the tip of the distal end of the primary radiation conductor. For this task there is in this case for the corresponding radiation source 9a at the proximal end of the particular diagnostic radiation conductor 17 a beamsplitter 18, which is preferably dichroitic, transmitting the exciting light but reflecting the red-shifted fluorescence light. This reflected light is focused into the proximal end of a conveying radiation conductor 19, the distal end of which is connected to the radiation sensor 12, which records the fluorescence light distribution. A suitable self-contained fluorosensor is described in Rev. Sci. Instr. 71, 3004 (2000).

By rotating the turnable disc 4, the fluorescence which is proportional to the concentration of the sensitizer, can be measured sequentially at the tips at the distal ends of the six primary radiation conductors. Since the sensitizer is bleached by the strong red treatment light, being particularly strong just around the tip of the primary radiation conductor 6', it is essential to make this measurement before the start of the treatment.

If the tips of the primary radiation conductors 6 in addition are treated with a material, the fluorescence properties of which are temperature dependent, sharp fluorescence lines are obtained upon excitation, and the intensity of the lines and their relative strength depend on the temperature of the tip of the radiation conductor 6'. Examples of such materials are salts of the transition metals or the rare earth metals. Thus also the temperature can be measured at the six positions of the six radiation conductors, one at a time. The measured temperatures can be utilized to find out if blood coagulation with an associated light attenuation has occurred at the tip of the radiation conductor 6 and for studies regarding the utilization of possible synergy effects between PDT and thermal interaction. Since the lines obtained are sharp, they can be lifted off the more broad-banded fluorescence distribution from the tissue.

The concentration of the sensitizer can for certain substances be measured in an alternative way. Then the red light used for the light propagation studies is used to induce near-infrared fluorescence. This fluorescence penetrates through the tissue to the tips of the receiving primary radiation conductors 6, and are displayed simultaneously as spectra obtained in the radiation sensor 12. A tomographic calculation of the concentration distribution can be performed based on in total thirty measurement values.

After diagnostic measurements and calculations have been performed, the primary fibers 6 optically coupled to the tissue of the patients can be utilized for therapy by rotation of the turnable disc 4 by 30 degrees. Referring to FIG. 7, the therapeutic radiation conductors 7b of every other secondary radiation conductor 7 is utilized, now connected to the opposing radiation conductors 6 via the distributor 1. Each or the six therapeutic radiation conductors 7b is connected to an individual therapeutic radiation source 9b, which preferably is a laser source with a wavelength which is adapted to the absorption band of the sensitizer. At the photodynamic tumor treatment a dye laser or a diode laser is preferably used, with a wavelength which is selected with regard to the sensitizer employed. For Photofrin® the wavelength is 630 nm, for δ amino levulinic acid (ALA) it is 635 and for phthalocyanines it is around 670 nm. The individual lasers are regulated during the treatment to a desirable individual output power. If desired, they may have built-in monitoring detectors.

The therapeutical treatment can be interrupted and new diagnostic data can be processed in an interactive method till an optimal treatment has been reached. This method can include synergy between PDT and hyperthermia, where an increased temperature is reached at increased fluxes of laser radiation. The whole process is controlled using a computer, which does not only perform all the calculations but also is utilized for regulation.

The invention claimed is:

1. A system for interactive interstitial photodynamic or photothermal tumor therapy and diagnosis, said system comprising:

at least one therapeutic radiation source and at least one diagnostic radiation source;

at least one diagnostic radiation sensor, and at least two primary radiation conductors which at their distal ends are interstitially arranged in tumor site, wherein the primary radiation conductors in use are employed as a transmitter for diagnostic radiation from said diagnostic radiation source for diagnosis of a tumor at said tumor site, or for therapeutic radiation from said therapeutic radiation source for therapy of the tumor, respectively, or as a receiver for conduction of radiation from the tumor site for diagnosis of the tumor; and a distributor for distribution of radiation from the diagnostic and therapeutic radiation source to the tumor site, and from the tumor site to at least one diagnostic radiation sensor, wherein the distributor comprises a plurality of primary radiation conductors arranged for conducting radiation to and from the tumor site, a plurality of secondary radiation conductors arranged for delivering radiation from the diagnostic or therapeutic radiation source or conduction of radiation to the diagnostic radiation sensor, two flat discs abutting against each other, wherein a first of said discs is fixed and the second of said discs is turnable relatively to the other disc, and wherein each disc has holes arranged on a circular line, wherein the proximal ends of the primary radiation conductors are fixed in the holes of the first disc and distal ends of the secondary radiation conductors are fixed in the holes of the second disc, whereby the primary and the secondary radiation conductors by rotation of the two discs relative another are connectable to each other in different constellations.

2. The system according to claim 1, wherein the circle radius of said circle line on one disc equals the circle radius on the other disc and where the holes in one disc are equally distributed on the circle line with an angular separation of v1=(360/n1) degrees, n1 being the number of holes, and the holes in the other disc are equally distributed on the circle line with an angular separation of v2=(360/n2) degrees, wherein n2=m×n1, and wherein m is a multiple, which yields n2 as an integer≧1.

3. A system according to claim 2, wherein n1 is the number of holes in the fixed disc of the distributor, n1=6 and m=2, yielding n2=12 holes in the turnable disc of the distributor.

4. A system according to claim 1 wherein every other secondary radiation conductor is part of a series of diagnostic radiation conductors and that a diagnostic radiation conductor in said series of diagnostic radiation conductors is arranged for emitting diagnostic radiation from the diagnostic radiation source and the other diagnostic radiation conductors in said series of diagnostic radiation conductors are arranged for conduction of radiation to the diagnostic radiation sensor.

5. A system according to claim 4, wherein the diagnostic radiation source comprises a diagnostic light source for white, red, blue/violet or ultraviolet light.

6. A system according to claim 5, wherein a beamsplitter is associated with the diagnostic light source for blue/violet or ultraviolet light.

7. A system according to claim 6, wherein the beamsplitter is a dichroic beamsplitter, and wherein the system additionally comprises a transferring diagnostic radiation conductor arranged between the dichroic beamsplitter and the diagnostic radiation sensor.

8. A system according to claim 7, wherein the same primary radiation conductor is configured to record fluorescence and to transmit diagnostic radiation to the tumor site.

9. A system according to claim 5, wherein the primary radiation conductors distal ends are treated by a material with temperature sensitive fluorescence emission.

10. A system according to claim 9, wherein the therapeutic radiation which in use is sent to the tumor site is configured to heat the tumor site, and wherein the intensity of the therapeutic radiation is controllable by a measured temperature in order to regulate the temperature of the tumor site at the individual primary radiation conductors.

11. A system according to claim 4, wherein the radiation sensor comprises a spectrometer with a two-dimensional detector array and the proximal ends of said other diagnostic radiation conductors of said series of diagnostic radiation conductors are arranged in the entrance slit of the spectrometer.

12. A system according to claim 1, wherein every other secondary radiation conductor is part of a series of therapeutic radiation conductors arranged for emission of therapeutic radiation from the therapeutic radiation source.

13. A system according to claim 1, wherein the therapeutic radiation source comprises a light source for coherent light of a single fixed wavelength.

14. A system according to claim 1, wherein the distributor is configured for locking the turnable disc into predetermined angular positions.

15. A system according to claim 1, wherein the radiation conductors are optical fibers.

16. A method for interactive interstitial photodynamic or photothermal tumor therapy and diagnosis, said method comprising:
    inserting at least two primary radiation conductors at distal ends thereof interstitially into a tumor;
    activating a diagnostic radiation source and transmitting diagnostic radiation through one of said primary radiation conductors to the distal ends thereof;
    transmitting the diagnostic radiation through tissue at said tumor site to distal ends of the remaining primary radiation conductors;
    collecting and evaluating diagnostic information from radiation received from said tumor;
    automatically switching between tumor therapy and tumor diagnostics; and
    controlling the tumor therapy by regulating a therapeutical radiation intensity depending on said diagnostic information.

17. The method according to claim 16, further comprising switching between tumor diagnostics and tumor therapy by rotating a turnable disc in an optical distributor, such that different arrangements of diagnostic and therapeutic radiation conductors are connected to the primary radiation conductors.

18. The method according to claim 17, further comprising alternatingly switching between interactive interstitial photodynamic tumor therapy, photothermal tumor therapy using hyperthermia, and tumor diagnostics during the same occasion of treatment of said tumor site.

19. The method according to claim 16, wherein said inserting the at least two primary radiation conductors at the distal ends thereof interstitially into the tumor comprises
    placing injection needles having a lumen in the tumor,
    moving the primary radiation conductors forward through the lumen of an injection needle to arrive outside the distal end of the needle, respectively, thereby fixing these primary radiation conductors in the tumor.

20. The method according to claim 16, further comprising using the same primary radiation conductors during treatment, for integrated diagnostics and dosimetry.

* * * * *